(12) United States Patent
Ciceri et al.

(10) Patent No.: US 8,106,231 B2
(45) Date of Patent: Jan. 31, 2012

(54) PROCESS FOR THE PREPARATION OF (2R,3S)-3-PHENYLISOSERINE METHYL ESTER ACETATE SALT

(75) Inventors: Daniele Ciceri, Milan (IT); Bruno Gabetta, Milan (IT); Nicola Vignola, Strengelbach (CH); Frieder Mitzel, Zürich (CH); Beat T. Weber, Zofingen (CH)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/527,887

(22) PCT Filed: Feb. 11, 2008

(86) PCT No.: PCT/EP2008/001015
§ 371 (c)(1),
(2), (4) Date: Feb. 3, 2010

(87) PCT Pub. No.: WO2008/101608
PCT Pub. Date: Aug. 28, 2008

(65) Prior Publication Data
US 2010/0168460 A1    Jul. 1, 2010

(30) Foreign Application Priority Data
Feb. 22, 2007    (EP) .................................... 07003642

(51) Int. Cl.
*C07C 229/00*    (2006.01)
(52) U.S. Cl. ....................................................... 560/37
(58) Field of Classification Search .................. None
See application file for complete search history.

(56) References Cited

U.S. PATENT DOCUMENTS

| | | | | |
|---|---|---|---|---|
| 2,275,378 | A * | 3/1942 | Johnson ........................ | 562/829 |
| 4,217,280 | A * | 8/1980 | Jarreau et al. ................. | 540/104 |
| 4,695,589 | A * | 9/1987 | Philion ......................... | 514/653 |
| 6,025,516 | A   | 2/2000 | Ramaswamy et al. | |
| 2006/0223886 | A1 * | 10/2006 | Dargazanli et al. ........... | 514/477 |
| 2008/0249310 | A1 * | 10/2008 | Kuilman et al. ................ | 546/82 |
| 2009/0093473 | A1 * | 4/2009 | Zimmermann et al. ... | 514/232.8 |

FOREIGN PATENT DOCUMENTS

| WO | WO2006/008170 | * | 1/2006 |
|---|---|---|---|
| WO | WO2006/134111 | * | 12/2006 |

OTHER PUBLICATIONS

Wuts et al., "Synthesis of (2R,3S)-isobutyl phenylisoserinate, The Taxol side chain, from ethyl benzoylacetate", Tetrahedron: Asymmetry 11(10):2117-2123, Year:2000.

Kearns et al., "Application of Yeast-Catalyzed Reductions to Synthesis of (2R,3S)-Phenylisoserine", Tetrahedron Letters 35(18):2845-2848, Year:1994.

Norman et al., "Principles of Organic Synthesis" Third Edition, Blackie Academic & Professional, 1993, p. 140.

\* cited by examiner

*Primary Examiner* — Daniel Sullivan
*Assistant Examiner* — Jennifer C Sawyer
(74) *Attorney, Agent, or Firm* — Porzio, Bromberg & Newman, P.C.

(57) ABSTRACT

A process for the enantioselective preparation of (2R,3S)-3-phenylisoserine methyl ester acetate salt of formula (I) which is an useful building block for the synthesis of taxane derivatives. The process involves the resolution of racemic threo-phenylisoserine amide and its conversion into (I).

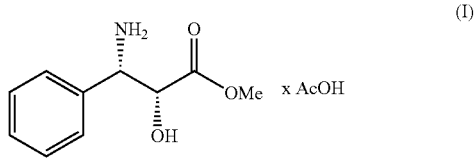

(I)

4 Claims, No Drawings

US 8,106,231 B2

PROCESS FOR THE PREPARATION OF (2R,3S)-3-PHENYLISOSERINE METHYL ESTER ACETATE SALT

CROSS REFERENCE TO RELATED APPLICATION

This is a National Stage of International Application PCT/EP2008/001015, filed 11 Feb. 2008, which claims the benefit of Application No. 07003642.1, filed in the EP on 22 Feb. 2007, the disclosures of which Applications are incorporated by reference herein.

FIELD OF INVENTION

The present invention relates to the semi-synthesis of taxanes, in particular to the preparation (2R,3S)-3-phenylisoserine methyl ester acetate salt (I)

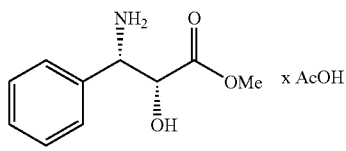

a useful building block for the synthesis Paclitaxel and Docetaxel.

BACKGROUND OF THE INVENTION

Paclitaxel (II) is a naturally occurring diterpenoid taxane present at low concentration in several species of the slow-growing yew tree (*Taxus* genus, Taxaceae family), which has been approved for the treatment of refractory advanced ovarian cancer, breast cancer and Kaposi's sarcoma.

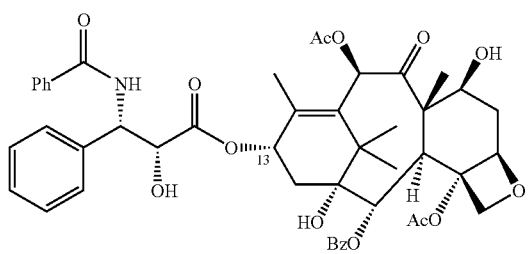

Docetaxel (III) is a synthetic diterpenoid taxane which has been approved for the treatment of breast cancer, locally advanced or metastatic non-small cell lung cancer (in combination with cisplatin) and prostate cancer (in combination with prednisone).

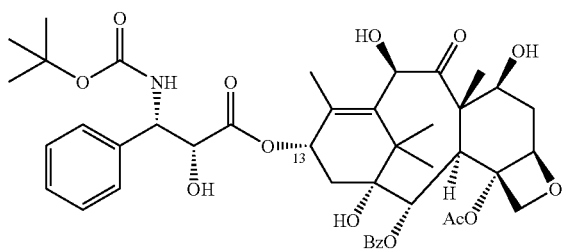

Due to the complex structure of the taxane nucleus, total synthesis of paclitaxel and docetaxel is very long and expensive, therefore it is not suitable for an industrial scale. So far, large-scale preparation of these compounds has been accomplished by semi-synthesis from appropriate starting materials, such as 10-deacetylbaccatine III (IV) (herein after referred to as 10-DAB III)

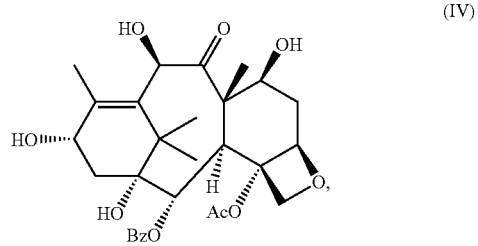

a biogenetic precursor of paclitaxel, and an enantiomerically pure precursor of the 3-phenyl-isoserinyl side-chain at C-13. US 2005/0049297, in the Applicant's name, discloses the reaction between 10-DAB protected at position 7 with a compound of formula (V)

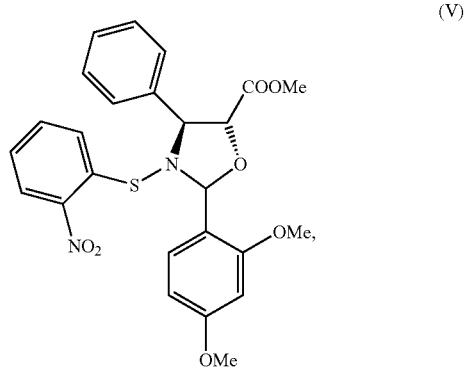

which is in turn prepared from (2R,3S)-3-phenylisoserine methyl ester acetate salt (I)

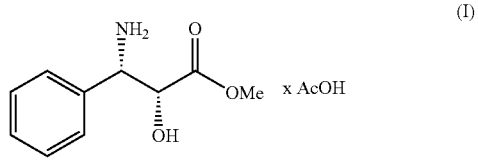

Compound (V) contains an easily removable nitrogen protecting group (the 2-nitrophenylsulfanyl moiety) and can therefore be used for the synthesis of both paclitaxel and docetaxel, which is indeed convenient from the industrial standpoint.

Methods for the synthesis of enantiomerically pure (2R,3S)-3-phenylisoserine methyl ester are reported in the literature.

*Natural Product Letters* vol. 6, pp. 147-152 discloses the reaction of benzaldehyde and chloroacetic acid methyl ester in the presence of sodium methoxide to give racemic trans 3-phenylglicidic acid methyl ester, which is converted to the racemic cis isomer via epoxide ring opening with gaseous HCl in benzene and subsequent epoxide closure by treatment with Amberlite 400 (OH⁻). The racemic cis-epoxide is then treated with KOH in ethanol to give the potassium salt which is added with HCl to liberate racemic cis-phenylglicidic acid.

Treatment with D-(+)-ephedrine provides a mixture of diastereomeric salts, wherefrom cis-(2R,3S)-3-phenylglicidic acid (+)- ephedrine salt can be recovered in 30% yield by fractional crystallisation with acetone. Acidic treatment of the ephedrine salt allows to obtain optically active phenylglycidic acid, which can be treated with ammonia to provide (2R,3S)-3-phenylisoserine acid. The scaling-up of this process is troublesome because, as also reported by the authors, cis-phenylglycidic acid is unstable and its optical resolution is successful only if carried out rapidly, which is generally very difficult to achieve on an industrial scale.

Synthetic Communications, 31 (23), 3609-3615 (2001) discloses a similar procedure for the obtainment of racemic cis-3-phenylglycidic methyl ester. Thereafter, the method comprises the treatment of racemic cis-3-phenylglycidic acid methyl ester with ammonia to obtain racemic threo-3-phenylisoserine amide, which is hydrolysed with barium hydroxide to racemic threo-3-phenylisoserine acid and benzoylated to give racemic threo-N-benzoyl-3-phenylisoserine acid. The racemic mixture is resolved by fractional crystallisation with S-(−)-methylbenzylamine to give (2R,3S)-N-benzoyl-3-phenylisoserine acid. This compound is not suitable for the production of (2R,3S)-3-phenylisoserine methyl ester (I), because the removal of the benzoyl group requires harsh conditions (i.e. 6 N HCl, reflux, 48 hours) and may affect the stereochemistry of the molecule.

In U.S. Pat. No. 6,025,516 racemic trans-3-phenylglicidic acid methyl ester is reacted with ammonia to produce racemic erythro-3-phenylisoserine amide which is treated with a resolving agent such as tartaric, dibenzoyltartaric, lactic, mandelic or camphorsulphonic acid to give a mixture of diastereomeric salts. (2S,3S)-3-Phenylisoserine amide can be recovered in enantiomeric pure form after recrystallisation from suitable solvents. However, the C-2 stereogenic center is still in the S-configuration and further steps are necessary for inversion of configuration: the amino group must be protected with an acetyl moiety and the 2-OH group must be converted into its methanesulfonic derivative to provide an oxazoline compound, which is treated with HCl in ethanol to give the desired (2R,3S)-3-phenylisoserine acid methyl ester.

Therefore, there is still the need for an improved process for the preparation of (2R,3S)-3-phenylisoserine methyl ester which overcomes the above-mentioned drawbacks.

DESCRIPTION OF THE INVENTION

The present invention relates to a process for the preparation of (2R,3S)-3-phenylisoserine methyl ester acetate salt (I)

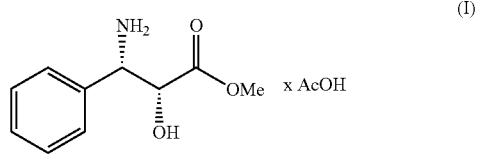

(I)

which comprises the following steps:
a) resolution of racemic threo 3-phenylisoserine amide (VI)

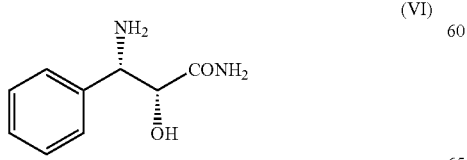

(VI)

with an enantiomerically pure organic acid to provide a corresponding acid salt of (2R,3S)-3-phenylisoserine amide;

b) treatment of the organic acid salt of (2R,3S)-3-phenylisoserine amide with a strong inorganic acid in a protic solvent to provide a (2R,3S)-3-phenylisoserine amide inorganic acid salt;

c) treatment of the (2R,3S)-3-phenylisoserine amide inorganic acid salt with hydrochloric acid in a protic solvent followed by treatment with acetic acid to crystallise (2R,3S)-3-phenylisoserine methyl ester acetate salt (I).

Step (a) is preferably carried out using enantiomerically pure (+)-tartaric acid or a derivative thereof, such as (−)-dibenzoyltartaric acid, in ethanol as solvent at the reflux temperature. (2R,3S)-3-Phenylisoserine amide hydrochloride and the salts of (2R,3S)-3-phenylisoserine amide with tartaric or dibenzoyltartaric acid are novel and are a further object of the present invention.

Step (b) is preferably carried out using sulfuric or hydrochloric acid in ethanol as solvent at a temperature between 40 and 45° C. The treatment with hydrochloric acid or sulfuric acid in step c) is preferably carried in methanol as solvent at room temperature and the crystallisation of the final product is preferably carried out using a mixture of ethyl acetate and heptane as solvent. (2R,3S)-3-Phenylisoserine methyl ester acetate salt (I) has an enantiomeric and chromatographic purity of more than 99.0%.

Racemic threo 3-phenylisoserine amide (VI) can be prepared as described, for example, in Synthetic Communications, 31 (23), 3609-3615 (2001), by treatment of racemic cis-3-phenylglicidic acid methyl ester (VIIa)

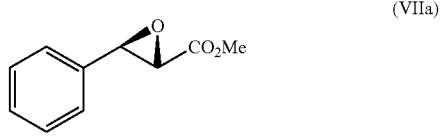

(VIIa)

with gaseous ammonia in methanol.

Racemic cis-3-Phenylglicidic acid methyl ester (VIIa) can in turn be prepared according to known methods, for example as described in Natural Product Letters vol. 6, pp. 147-152. According to a preferred embodiment of the invention, after Darzen's reaction between benzaldehyde and chloroacetic acid methyl ester to form racemic trans-3-phenylglicidic acid methyl ester (VIIb)

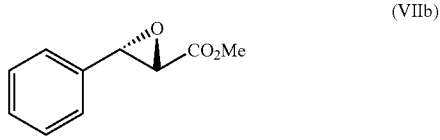

(VIIb)

compound (VIIb) is treated with an anhydrous hydrohalic acid in an aromatic aprotic solvent to give a racemic threo halohydrin (VIII)

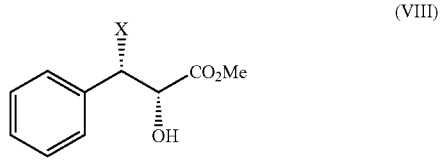

(VIII)

wherein X represents a halogen atom which is converted to compound (VIIa) by treatment with an organic or inorganic base, preferably sodium carbonate in water.

The process of the invention is particularly advantageous from the industrial standpoint, since it allows to directly carry out the resolution of threo-phenylisoserine amide in a simpler manner than the processes of the prior art, in particular the process of U.S. Pat. No. 6,025,516, which requires inversion of configuration of the stereogenic center at the 2-position.

The following examples illustrate the invention in greater detail.

EXAMPLES

Preparation 1

Racemic 3-Bromo-2-hydroxy-3-phenyl-propionic acid methyl ester (Reference Example)

A mixture of benzaldehyde (212.0 g, 2.0 moles) and methyl chloroacetate (282.0 g, 2.6 mole) in methanol (320.0 g) was cooled to 0° C. under nitrogen. Sodium methoxide (466.0 g of a 30 wt % solution in methanol, 2.5 moles) was added over a period of 2 hours and the mixture was stirred for further 60 minutes at 0° C. The mixture was then allowed to reach 22° C. and stirred for further 2 hours at this temperature. After slow addition of acetic acid (30.0 g, 0.5 moles), toluene (465.0 g) and water (670.0 g) were added consecutively. The aqueous phase was separated and the organic layer was distilled in order to remove water and methanol. After removal of 170.0 g of distillate the mixture was allowed to cool to 25° C. HBr (120.0 g, 1.5 moles) was added over a period of 4 hours keeping the temperature at 25° C. After completion of the addition a mixture of 15.0 g of sodium bicarbonate in 300.0 g water was added dropwise, keeping the temperature between 25 and 30° C. The aqueous layer was then separated, toluene (175.0 g) was added and 115.0 g of toluene was distilled off in order to remove moisture. The mixture was cooled down to 20° C. and toluene (115.0 g) and heptane (260.0 g) were added consecutively. After seeding with 0.5 g of racemic 3-bromo-2-hydroxy-3-phenyl-propionic acid methyl ester, the mixture was slowly cooled to 0° C. and stirred for further 3 hours. The precipitated product was filtered off, washed with 200.0 g heptane and vacuum dried at 45° C. Yield: 234.0 g (0.9 mole, 45%).

$^1$H NMR CDCl$_3$ (δ): 3.23 (1H), 3.79 (3H), 4.40 (1H), 5.31 (1H), 7.22 (3H), 7.48 (2H).

Preparation 2

Racemic cis-3-phenylglicidic methyl ester (Reference Example)

Racemic 3-bromo-2-hydroxy-3-phenyl-propionic acid methyl ester (VII) (259.1 g, 1.0 mole) was suspended in water (700.0 g) and the mixture was heated up to 50° C. A solution of sodium carbonate (112.4 g) in water (660.0 g) was slowly added over a period of 1 hour. The mixture was stirred for further 60 minutes and toluene (365.0 g) was added allowing the mixture to cool down to room temperature. The aqueous layer was separated and the organic residue was washed with water (180.0 g). The organic layer was separated and concentrated in vacuo yielding the product as an oil. Yield: 157.4 g (0.88 mole, 88%).

$^1$H NMR CDCl$_3$ (δ): 3.58 (3H), 3.83 (1H), 4.290 (1H), 5.01 (3H), 7.39 (5H).

Preparation 3

Racemic threo 3-phenylisoserine amide (Reference Example)

Racemic cis-3-phenylglicidic methyl ester (VIII) (430.0 g, 2.41 moles) was dissolved in methanol (2000.0 g) then 400.0 g of gaseous ammonia (23.5 moles) was added slowly keeping the temperature at 25° C. and the mixture was heated up to 60° C. and stirred for further 18 hours. The resulting suspension was then cooled to 10° C. and stirred for further 60 minutes. The product was filtered off, washed with 200.0 g of methanol and vacuum dried at 55° C. Yield: 324.4 g (2.1 moles, 75%).

$^1$H NMR d$_6$-DMSO (δ): 1.79 (2H), 3.88 (1H), 4.12 (1H), 5.35 (1H), 7.25 (7H).

Preparation 4

(2R,3S)-3-Phenylisoserine amide dibenzoyl-tartaric acid salt

Racemic threo 3-phenylisoserine amide (IX) (120.0 g, 0.67 mole) and (−)-dibenzoyltartaric acid (240.1 g, 0.67 mole) were suspended in ethanol (1080.0 g). The suspension was refluxed for 2 hours, then cooled to room temperature and stirred for further 60 minutes. The product was filtered off, washed with ethanol (400.0 g) and vacuum dried at 50° C. Yield: 180.6 g (0.34 mole, 50%).

$^1$H NMR CD$_3$OD (δ): 4.36 (1H), 4.55 (1H), 5.92 (2H), 7.42 (91H), 7.63 (2H), 8.15 (4H).

Preparation 5

(2R,3S)-3-Phenylisoserine amide hydrochloride (2R,3S)-3-Phenylisoserine amide dibenzoyl-tartaric acid salt (X) (180.6 g, 0.34 mole) was suspended in ethanol (535.0 g) and the mixture was heated to 42° C. 46.2 g of concentrated hydrochlorid acid (32%) was then slowly added to the suspension keeping the temperature at about 45° C. After completion of the addition the mixture was cooled down to 0° C. over a period of 1 hour and stirred for 1 further hour. The product was filtered off, washed with ethanol (100.0 g) and vacuum dried at 80° C. Yield: 60.5 g (0.28 mole, 82.0%).

$^1$H NMR d$_6$-DMSO (δ): 4.21 (1H), 4.39 (1H), 6.57 (1H), 7.40 (5H), 8.54 (3H).

Preparation 6

(2R,3S)-3-Phenylisoserine methyl ester acetate (I)

(2R,3S)-3-Phenylisoserine methyl ester hydrochloride (XI) (20.0 g, 0.092 mole) was suspended in methanol (140.0 g). 7.0 g gaseous HCl was slowly added keeping the temperature at about 25° C. After completion of the addition the mixture was heated at reflux for further 3 hours. After distilling off 85.0 g of methanol the mixture was cooled down to room temperature. After the addition of 220.0 g ethyl acetate 20.0 g of triethyl amine (0.2 mole) was added, keeping the temperature at 25° C. After distillation of 195.0 g of solvent further 195.0 g ethyl acetate were added. The suspension was filtered at 50° C. and the residue was washed with 50.0 g ethyl acetate. The filtrate was cooled to 40° C. and 9.0 g of acetic acid (0.15 mole) were added slowly until formation of a precipitate. The mixture was cooled down to 0° C. and stirred for further 2 hours. The product was filtered off, washed with 30.0 g ethyl acetate and vacuum dried at 50° C. Yield: 20.3 g (0.08 mole, 87%).

$^1$H NMR d$_6$-DMSO (δ): 1.89 (3H), 3.52 (3H), 4.09 (2H), 5.01 (3H), 7.31 (5H).

The invention claimed is:
1. A process for the preparation of (2R,3S)-3-phenylisoserine methyl ester acetate salt (I)

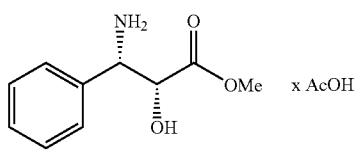

which comprises the following steps:
a) treatment of racemic threo 3-phenylisoserine amide (VI)

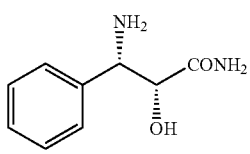

with an enantiomerically pure organic acid to provide a corresponding acid salt of (2R,3S)-3-phenylisoserine amide;
b) treatment of the acid salt of (2R,3S)-3-phenylisoserine amide with a strong inorganic acid in a protic solvent to provide a (2R,3S)-3-phenylisoserine amide inorganic acid salt;
c) treatment of the (2R,3S)-3-phenylisoserine amide inorganic acid salt with hydrochloric acid in a protic solvent followed by treatment with acetic acid to crystallise (2R,3S)-3-phenylisoserine methyl ester acetate salt (I).

2. A process according to claim 1 wherein the solvent is ethanol.

3. A process according to claim 1 wherein step b) is carried out using sulfuric or hydrochloric acid in ethanol as solvent.

4. A process according to claim 1 wherein the protic solvent of step c) is methanol and (2R,3S)-3-phenylisoserine methyl ester acetate salt (I) is crystallized from a mixture of ethyl acetate and heptane.

* * * * *